United States Patent [19]
Grothues-Spork et al.

[11] Patent Number: 5,713,906
[45] Date of Patent: Feb. 3, 1998

[54] ENDOPROSTHESIS CUTTING-OFF DEVICE

[75] Inventors: Matthias Grothues-Spork, Berlin; Clemens Scholz, Freiburg; Thorsten Ahrens, Seitingen-Oberflacht, all of Germany

[73] Assignee: Ueth & Haug GmbH, Tuttlingen, Germany

[21] Appl. No.: 553,391
[22] PCT Filed: May 4, 1994
[86] PCT No.: PCT/EP94/01421
  § 371 Date: Feb. 13, 1996
  § 102(e) Date: Feb. 13, 1996
[87] PCT Pub. No.: WO94/26176
  PCT Pub. Date: Nov. 24, 1994

[30] Foreign Application Priority Data
May 15, 1993 [DE] Germany .......... 43 16 358.0

[51] Int. Cl.⁶ .................................. A61B 17/92
[52] U.S. Cl. .......................... 606/99; 606/86
[58] Field of Search .................. 606/86, 84, 99, 606/10; 30/164.5, 164.6, 164.7, 164.8, 168

[56] References Cited

U.S. PATENT DOCUMENTS

| | | | |
|---|---|---|---|
| 289,738 | 12/1883 | Wiedersheim | 30/164.7 |
| 1,384,330 | 7/1921 | Moshier | 81/490 |
| 2,655,921 | 10/1953 | Haboush | |
| 3,803,667 | 4/1974 | Rose | 606/1 |
| 4,586,496 | 5/1986 | Keller | 606/84 |
| 4,905,374 | 3/1990 | Schlein | |
| 5,019,083 | 5/1991 | Klapper | |

FOREIGN PATENT DOCUMENTS

| | | |
|---|---|---|
| 0 157 172 | 2/1985 | European Pat. Off. . |
| 0 549 362 | 6/1993 | European Pat. Off. . |
| 23 56 699 | 2/1973 | Germany . |
| 87 15 836 | 6/1988 | Germany . |
| 93 08770 | 5/1993 | WIPO . |

Primary Examiner—Michael Buiz
Assistant Examiner—David O. Reip
Attorney, Agent, or Firm—Antonelli, Terry, Stout, & Kraus, LLP

[57] ABSTRACT

Disclosed is a device for removing a prosthesis having a shaft engaged in a bone cavity. The device includes an elongated chisel blade having a cutting edge at its front end, and slidably disposed and longitudinally supported by a body and extending beyond a front face of the body. A driving-in member which, e.g., can be impacted by a hammer is removably coupled to the chisel blade and has an engaging pin attached thereto, the body having a free space for accepting this engaging pin, which engaging pin can extend through at least one engaging point in the chisel blade, so as to provide the chisel blade stably attached to the body while being easily removable therefrom. Various blades, of different thicknesses, can be utilized as part of the device. The body can have at least one circumferential rib to facilitate holding the device, and can have a handle extending in a direction perpendicular to the direction that the chisel blade extends. The driving-in member can include an impact collar, which can have an impact plate thereon, to be impacted by a hammer. Through use of the device of the present invention, a prosthesis can be removed simply and with little force, while causing as little trauma as possible.

34 Claims, 7 Drawing Sheets

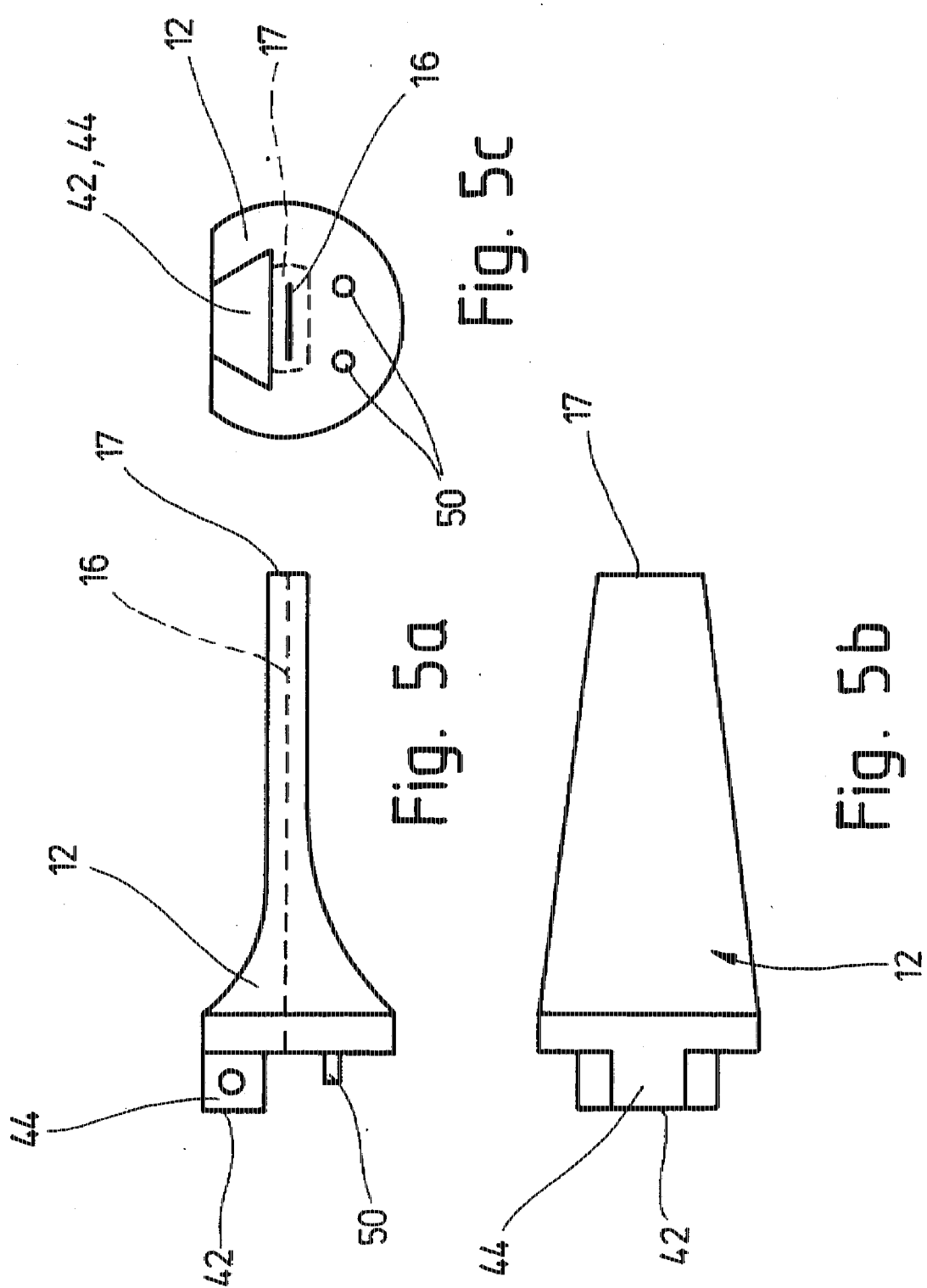

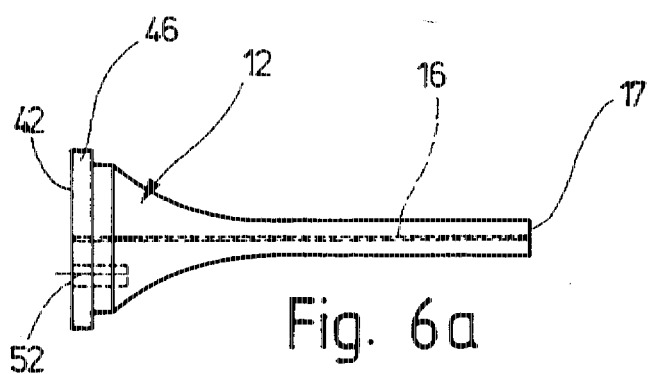
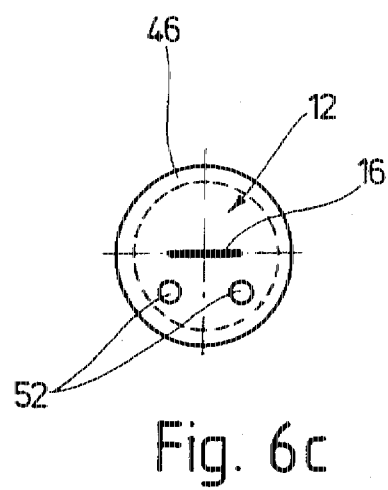
Fig. 6a
Fig. 6c
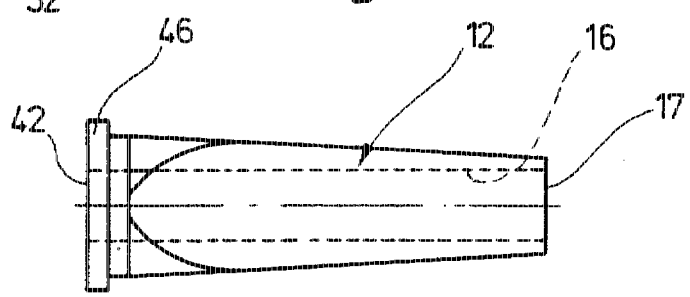
Fig. 6b
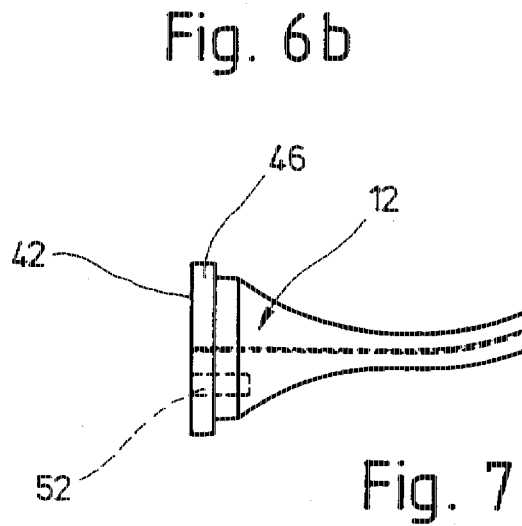
Fig. 7
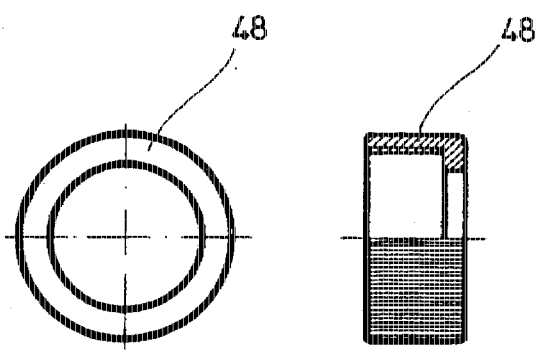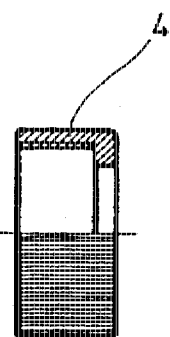
Fig. 8a    Fig. 8b

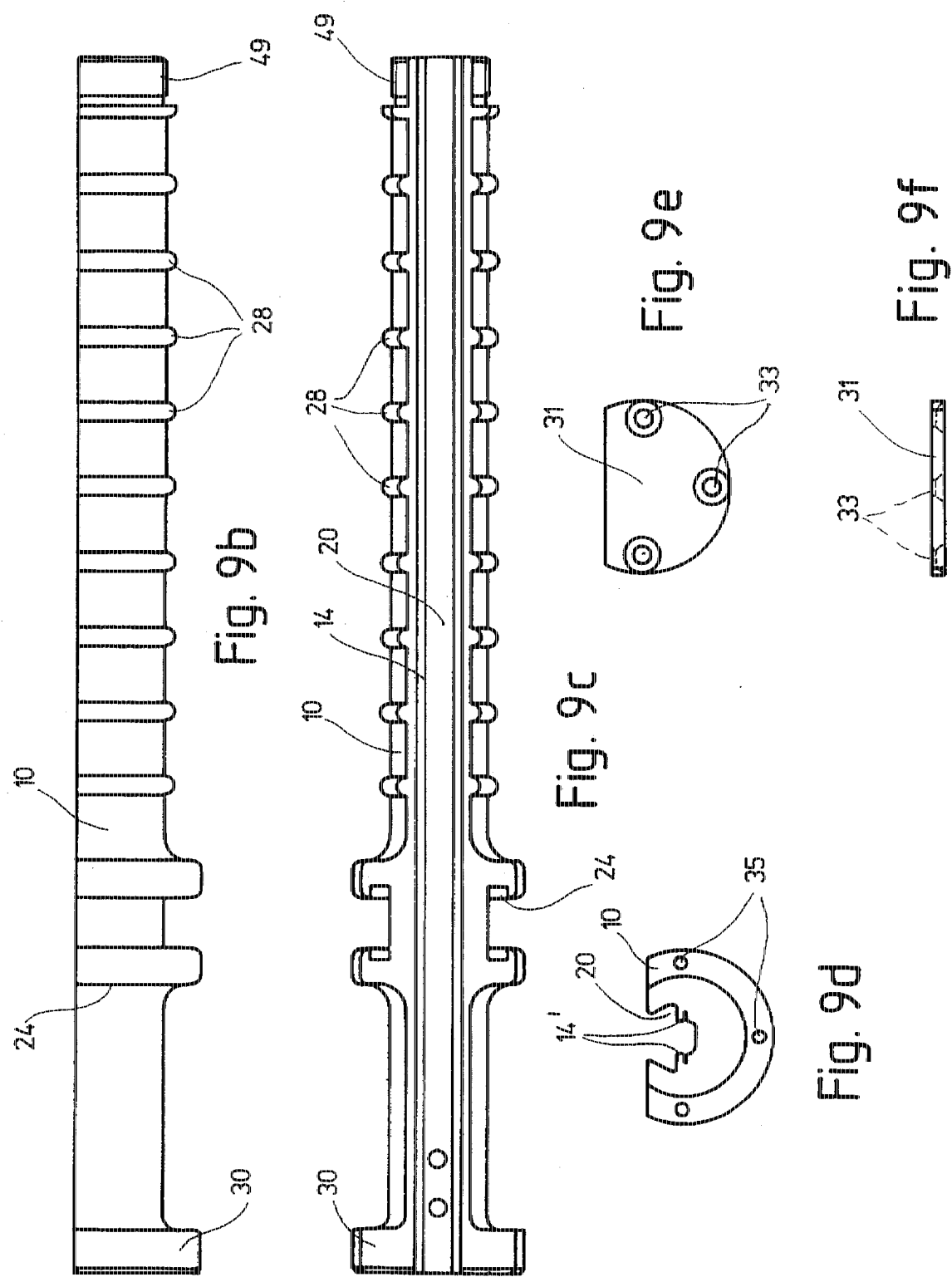

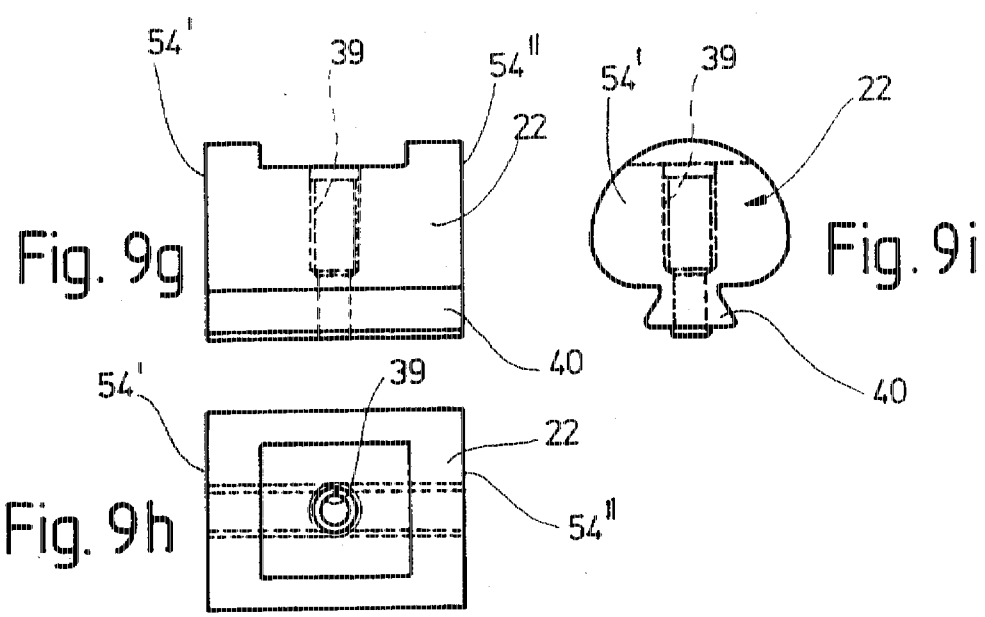
Fig. 9g   Fig. 9i
Fig. 9h
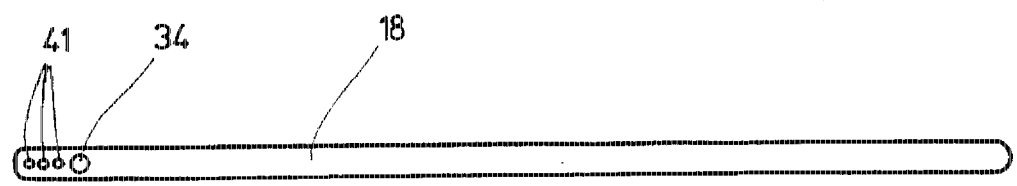
Fig. 10a
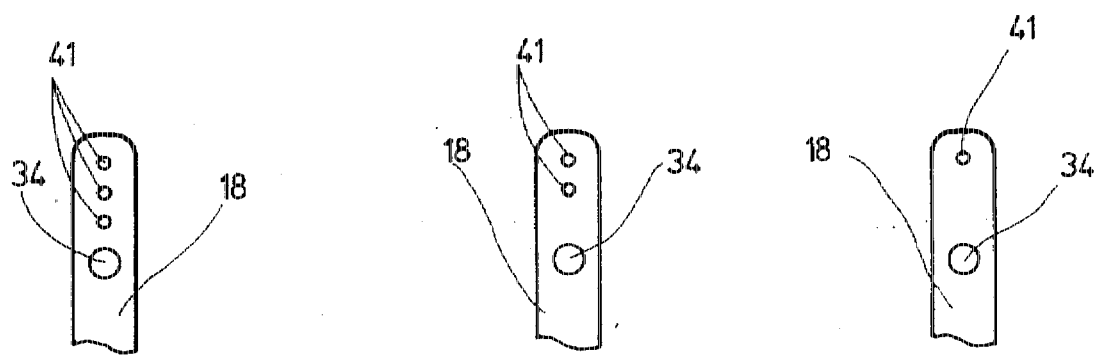
Fig. 10d   Fig. 10c   Fig. 10b

ENDOPROSTHESIS CUTTING-OFF DEVICE

BACKGROUND OF THE INVENTION

The invention relates to a device for removing endoprostheses having a shaft engaged in a bone cavity and coupled therein to the bone by a boundary layer made of bone tissue, connective tissue and/or cement.

Endoprostheses of this type are mainly hip prostheses, knee prostheses, elbow prostheses, shoulder prostheses, and ankle prostheses. The prostheses may for instance be mounted in the bone by using a cement such as polymethylmethacrylate (PMMA) or be mounted without using cement. When using cement-free prostheses the shaft of the prosthesis has a surface structure into which the bone tissue in the form of spongiosa is incorporated, thereby forming a solid connection between the bone and the prosthesis. On the other hand, after a certain time there is often a loosening of the prosthesis, due for instance to implantation errors, to short- or long-time infections or to fracturing of the prosthesis or bone. The durability of a first implant is typically ten to twenty years in the case of hip prostheses, in the case of knee prostheses approximately five to ten years. In the case of loosening a revision of the prosthesis is necessary. For this, the prosthesis has to be cut off from its anchoring in the bone cavity and pulled out of its anchoring. To this end, it is known to grip the prosthesis at its free proximal end or in holding means (e.g. holes) especially provided for this, and to remove the prosthesis, for instance by striking with a hammer. Especially in the case of cement-free endoprostheses this process of removal is very difficult, since the connection of the prosthesis to the bone is effected by a multitude of thin spongiosa, each of which may have a small strength, the entirety of which may often make a removal impossible, though. In these cases, but also in cases in which a part of the cement encasing is still strong when using cemented endoprostheses, the bone has to be split or fenestrated in order to weaken its connection to the prosthesis, before the prosthesis may be removed. These mechanical operations lead to a significant trauma of the bone bearing up to fracturing, which makes the revision of the prosthesis difficult and which prolongs the recuperation. This holds even more so for the renewal of revision prostheses, which are longer than the primary prostheses, and during the first revision of which there may already have occurred a loss of bone matter.

SUMMARY OF THE INVENTION

Based on this, it is the object of the invention to develop a device of the type described above, with which the prostheses can be removed while causing as little trauma as possible, so that the removal of the prostheses may be performed simply and with little force.

In order to achieve this object, the combination of features of patent claim 1 is suggested. Advantageous embodiments and further developments of the invention result from the dependent claims.

The solution according to the invention is based on the idea that by driving a flexible chisel blade into the boundary layer between the endoprosthesis and the bone bearing the chisel blade may be guided such that it runs precisely along the surface of the prosthesis, without entering and damaging the surrounding bone or becoming wedged with the prosthesis. The boundary layer consisting of spongiosa or connective tissue structures or cement is separated during this, so that after repeated driving in-over the circumference of the prosthesis the desired removal results. In order to make this possible, the removing device according to the invention has a body having an impact surface on its front face, an elongated chisel blade having a cutting edge at its front end which is guided in a thrust slide of the body and is disposed longitudinally slidable beyond the front face of the body, and a driving-in member which is removably coupleable to the chisel blade and longitudinally slidable along the body parallel to the thrust slide.

According to a preferred embodiment of the invention the chisel blade is made of a flexible flat strip of tough, resilient material, for instance of a flat strip of resilient stainless steel. In order to achieve an optimal fit with respect to the shaft surface of the endoprosthesis to be removed, the flat strip may have a bend or wave contour perpendicular to its longitudinal extension. In this case, the chisel blade may consist of a shape memory alloy, especially a nickel-titanium alloy or of a resilient synthetic material. In order to ensure the necessary flexibility, the chisel blade has a thickness of 0.2 to 0.6 mm. Chisel blades having different thicknesses may for instance be distinguished by a thickness coding preferably fashioned as a bore pattern close to the proximal end. If necessary, the chisel blade may be of varying thickness in the transverse and/or longitudinal direction.

In a preferred embodiment of the invention the chisel blade has at least one engaging point preferably formed to be an opening for an engaging pin attached to the driving-in member. In order to simplify a change of blades, the engaging pin on the driving-in member is preferably coupleable and decoupleable to and from the chisel blade externally. To this end, the engaging pin may be formed by the tip of a screw which is guided in an internal screw thread of the driving-in member and which is actuatable externally, wherein the screw may have a knurled head which is disposed recessed in an open-edged opening of the driving-in member and accessible from two diametrically opposed sides.

Depending on the specific application, the cutting edge at the front end of the chisel blade can be slanted or curved. Especially for removing relatively long revision prostheses it can be advantageous that the chisel blade is longer than the body and that it has a multitude of engaging points for the engaging pin spaced in the direction of its longitudinal extension.

In a preferred embodiment of the invention the thrust slide has at least two mutually opposed guide surfaces which abut the two broadside faces and the two lateral side edges of the chisel blade. In particular, the thrust slide may be formed at least partially by two slit-like grooves which face each other with their openings and each of which embraces one lateral side edge of the chisel blade.

Advantageously, the driving-in member is guided by a thrust slide of the body, which is disposed parallel to the thrust slide of the chisel blade and has at least one impact area, the surface normal of which extends parallel or slanted with respect to the driving-in direction. The thrust slide of the driving-in member may then be formed to be a dovetail guide or a flat-bed guide, wherein a free space for accepting the engaging pin in the body may be disposed at the side of the chisel blade opposing the driving-in member. While the body consists of metal, especially of stainless steel, for reasons of stability, it is advantageous that the driving-in member is made of an impact-resistant and steam-sterilizable synthetic material, preferably of POM.

During the driving-in of the chisel blade the body rests on the prosthesis and/or on a front face of the bone with its tip-sided stop surface. It is therefore advantageous to shape the tip of the body relatively narrow and possibly curved under consideration of the anatomic condition, and to roughen the front face of the tip in a preferably criss-cross fashion. Further, it often occurs during the driving-in of the relatively thin chisel blade that it is worked past the elastic limit of the blade material and permanently deformed. It has therefore proven to be advantageous to provide the body with an exchangeable tip which has a guide channel for the chisel blade and whose front face forms a stop and abutting surface, which may be curved in the driving-in direction preferably toward the side of the body facing the driving-in member and which forms a stop for the driving-in member at its body-sided end. The exchange of the tip and the chisel blade is made easier when the tip can be clamped to the front face of the body by way of a coupling ring preferably having a multiple thread, if necessary with the inclusion of an elastomeric friction member.

In order to be able to hold the body with one hand without slipping while driving in the blade, the body has at least one circumferential rib extending at least partially over its circumference. Further, the body has an impact collar protruding over the surface of the body close to the end opposed to the tip, the impact collar being subjectable to strikes with a hammer in the direction of removal. Since the action of the hammer causes deformations of the impact collar, it is advantageous to provide the impact collar with an interchangeable impact plate preferably made of metal or an impact-resistant synthetic material. The impact plate may at the same time be formed to be a rear thrust slide cover and a stop for the chisel blade and the driving-in member. For the driving-in a recoil-damped hammer is advantageously used, which, to this end, may be filled with steel balls and have impact surfaces made of an impact-resistant synthetic material.

For a further improvement of the handling, a handle protruding generally perpendicularly over the surface of the body may be disposed on the body removably attachable and preferably adjustably over a part of the circumference of the body, the handle being hollow in order to save weight.

BRIEF DESCRIPTION OF THE DRAWINGS

In the following, the invention is further described with the aid of embodiments schematically shown in the drawing, in which

FIG. 5a to c show a side view, a top view and a rear end view of the tip according to FIG. 1;

FIG. 6a to c show a side view, a top view and a rear end view of a modified tip;

FIG. 7 shows a side view of a tip modified with respect to FIG. 6a;

FIG. 8a and b show a top view and a partially sectioned side view of a coupling ring for clamping the tip according to FIGS. 6 and 7 to the free end of the body;

FIG. 9b to d show a side view, a top view and a rear end view of the body of the cutting-out device according to FIG. 9a;

FIG. 9e and f show a broad side view and a small face view of the impact plate of the cutting-out device according to FIG. 9a;

FIG. 9g to i show a side view, a top view and a front end view of the driving-in member of the cutting-out device according to FIG. 9a;

FIG. 10a shows a broadside view of a chisel blade;

FIG. 10b to d show a detail from FIG. 10a in an enlarged representation with different thickness encodings.

DESCRIPTION OF THE PREFERRED EMBODIMENTS

Figure 1:
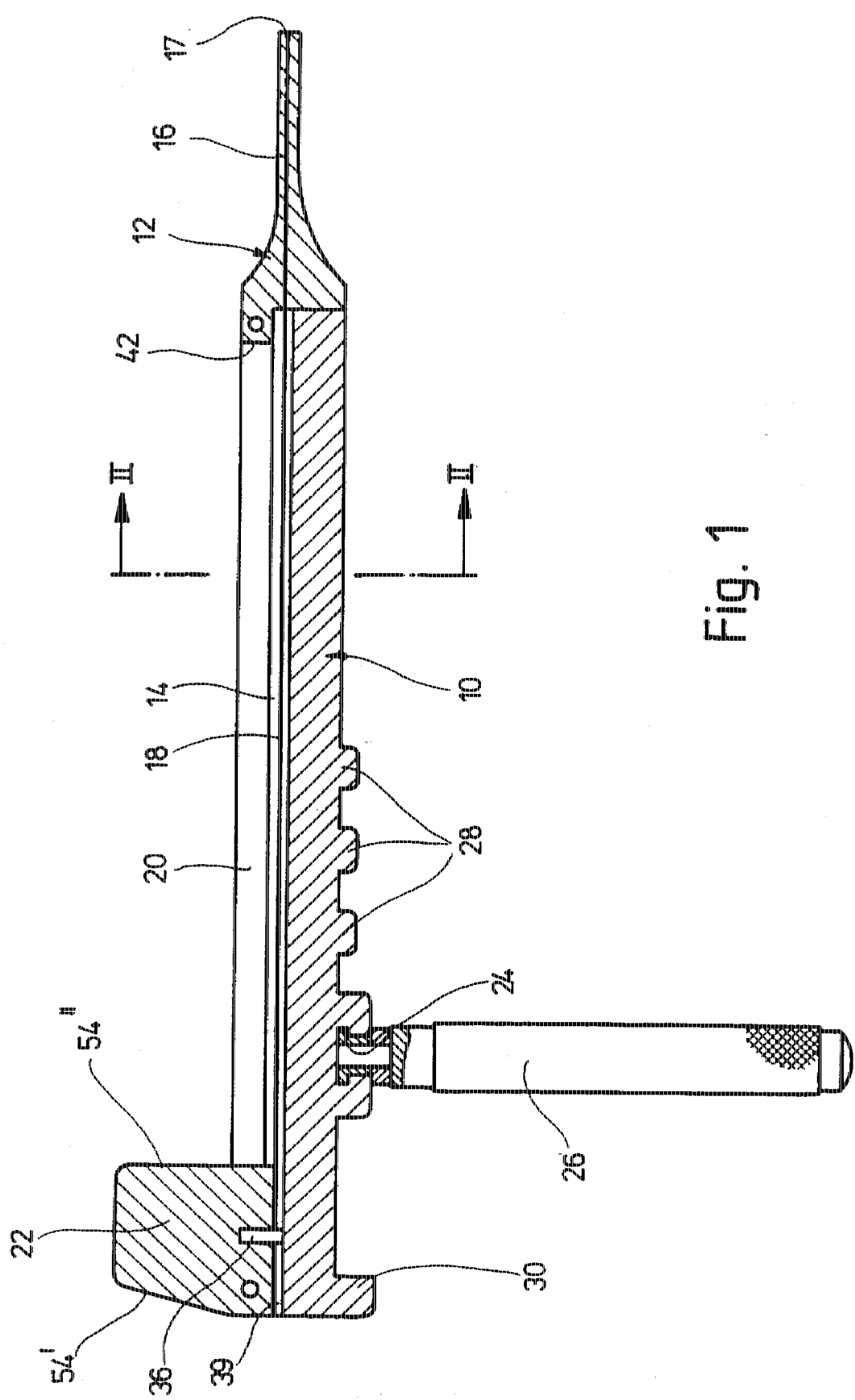
FIG. 1 shows a longitudinal section through a cutting-out device for endoprostheses.
Figure 2:
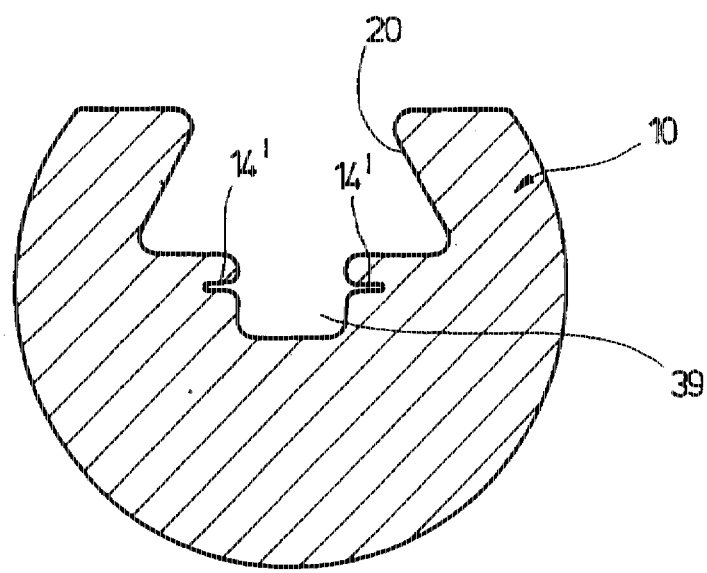
FIG. 2 shows a section along the line II—II in FIG. 1 without the tip and chisel blade in an enlarged representation.

The chisel devices shown in the drawing are used for cutting-out endoprostheses from their bone bearing. The devices mainly consist of an elongated guiding and holding body 10 designated "body" above and in the following, a tip 12 removably coupleable to one end of the body 10, a chisel blade 18 longitudinally guided in a thrust slide 14, 16 of the body 10 and the tip 12, a driving-in member 22 longitudinally guided in a guide channel 20 of the body, and a handle 26 which is removably coupleable in an undercut circumferential groove 24 of the body 10 and which is preferably hollow. In order to be able to safely hold the body 10 during the driving-in process, it is provided with a multitude of circumferential ribs 28 protruding over its surface area. At its rear end the body 10 additionally has an impact collar 30 which can be acted upon with a hammer. Shown in FIG. 1 is a mechanical vibrator or ultrasonic transducer 61 coupleable to the driving-in member 22 to provide a force acting in the direction that the chisel device is driven, or acting in a perpendicular direction to the direction that the device is driven. In the embodiment shown in FIG. 9a, the body 10 is additionally outfitted with an impact plate 31 located at the free rear surface of the impact collar 30, the impact plate 31 being screw-mounted with three flat-head bolts extending through the bores 33 into the threaded bore holes 35 of the body. The impact plate 31, which is made of metal or an impact-resistant synthetic material, at the same time serves as a rear cover for the thrust guides 14, 20, and thereby ensures that the driving-in member 22 and the chisel blade 18 are stopped at the rear end of the body 10 and cannot accidentally be knocked-out rearward from the body 10.

For strength reasons the body 10 suitably consists of stainless steel, while the driving-in member 22 is made of an impact-resistant synthetic material, especially from POM, for tribological reasons. The driving-in member 22 has one impact area 54', 54" at its front as well as at its rear end, the surface normal of the impact area being aligned slanted or parallel to the driving-in direction.

Figure 3:
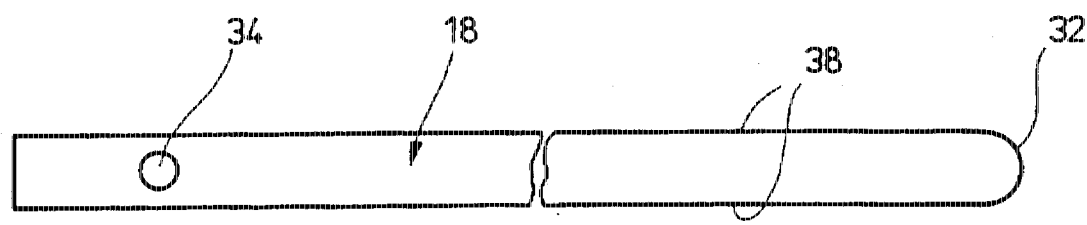
FIG. 3 shows a top view of a chisel blade.
Figures 4A, 4B:
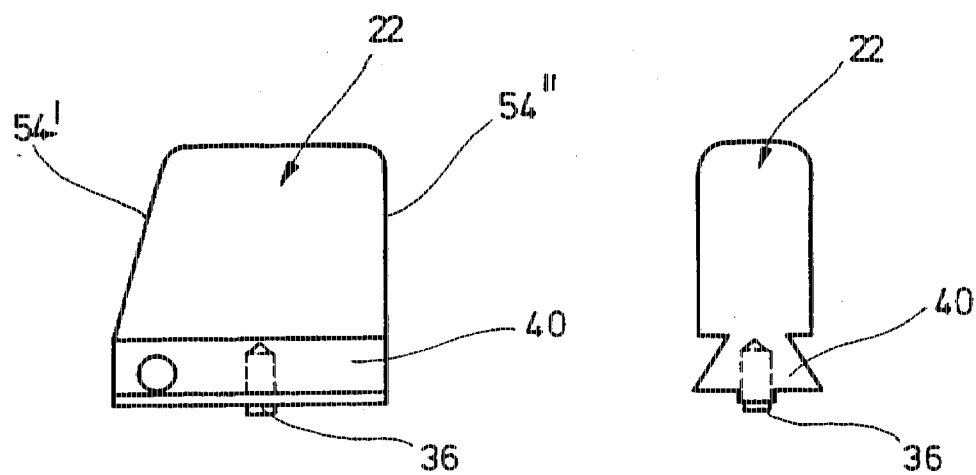
FIG. 4a and b show a side view and a front end view of the driving-in member according to FIG. 1.
Figure 9A:
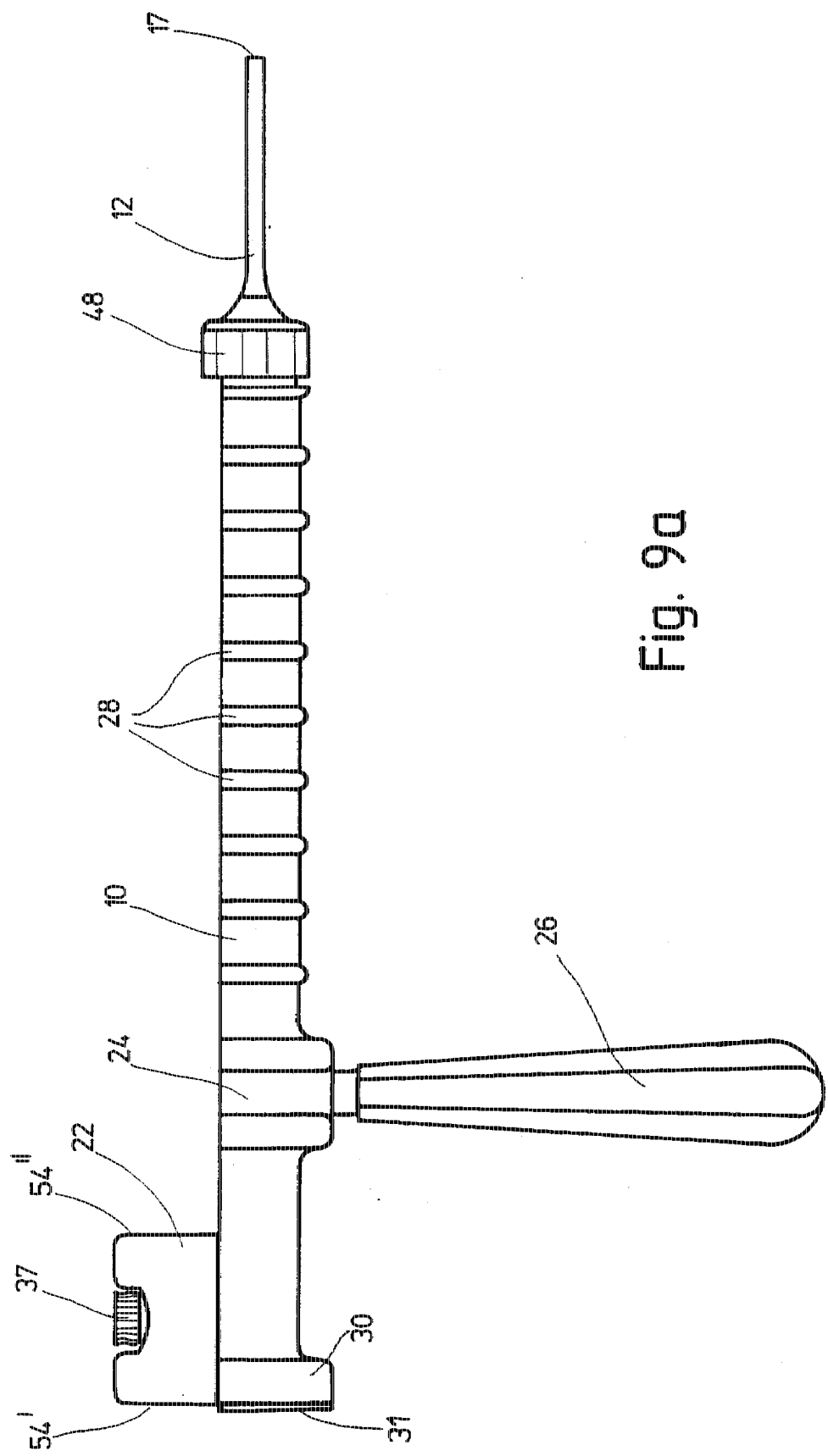
FIG. 9a shows a side view of a modified embodiment of a device for cutting out endoprostheses.

As can be seen especially from FIG. 3, the chisel blade 18 is formed to be a flexible flat strip, preferably made of resilient stainless steel having a thickness of 0.2 to 0.6 mm, which has a convexly curved cutting edge 32 at its tip and which has at least one opening 34 provided for engaging with an engaging pin 36 protruding downward from the driving-in member 22. In order to make the replacement of blades easier, the engaging pin 36 may be a manually actuatable holding notch (FIG. 4a, b) or an externally accessible screw having a knurled head 37, which is guided in an internal screw thread 39 of the driving-in member 22 (FIG. 9a, g, h, i). During the expulsion process the correct choice of the blade thickness is of decisive importance. Therefore, chisel blades having different thicknesses are available to the surgeon, which the surgeon can distinguish by the use of a suitable encoding, for instance in the form of different bore patterns 41 at the end of the blade (FIG. 10a to d).

The thrust slide 14 for the chisel blade 18 is formed by two grooves 14' which are formed into the body 10 in a mirror-inverted fashion with respect to each other and the openings of which face each other, the grooves embracing the chisel blade 18 at its lateral edges 38. The thrust slide 14 merges outwards into the dovetail guide channel 20 for the driving-in member 22, which for this reason has a diagonally undercut sliding block 40. The guide channel 20 for the driving-in member 22 terminates at the rear end of the tip 12, which forms a stop 42 for the driving-in member 22. In the embodiment shown in FIGS. 1 and 5a to c the tip 12 is engaged in the dovetail guide 20 of the body 10 by means of a formed part 44, while in the embodiments shown in FIGS. 6a to c, 7, and 8a and b the tip 12 is clamped to the face of the body 10 by means of a coupling ring 48 which may have a multiple screw thread 49. The thrust slide 14 for the chisel blade 18 merges into the thrust slide 16 at the tip 12 and is formed to be a slit opening for the passage of the chisel blade 18. The pins 50 and dead eyes 52, respectively, serve to fulfill a locking function of the tip 12 with respect to the body 10. For the dissection of the endoprosthesis first the proximal part of the prosthesis is exposed so that the junction with the bone bearing is freely accessible from the outside. Then the chisel device is put against the head of the prosthesis and the bone with the front face stop 17 of its tip 12 while the chisel blade 18 is retracted or protrudes approximately 10 mm over the front face, so that the cutting edge 32 of the chisel blade 18 is directed toward the bare junction. The chisel blade is then successively driven into the boundary layer between the shaft of the prosthesis and the bone by hammering on the impact area 54' of the driving-in member 22. Thereby the bone tissue and connective tissue adhering to the shaft of the prosthesis is gradually dissected up to the tip of the shaft, wherein the guidance of the flexible chisel blade is performed by the metallic shaft of the prosthesis. For the cutting-out of a prosthesis a multitude of driving-in processes of this type distributed over the circumference of the shaft of the prosthesis are necessary. In order to retract the chisel blade from the gap between the prosthesis and the bone either the driving-in member 22 in the region of its impact surface 54" or the body 10 in the region of the impact collar 30 are subjected to hammer strikes in the direction of removal. Since the chisel blade 18 has to overcome considerable resistances during the driving-in, which may lead to a plastic deformation, the chisel blade has to be replaced before almost each driving-in process. These replacements are made easier, when the tip 12 is removable and the engaging pin 36 of the driving-in member 22 is formed to be a holding notch or a screw.

In summary, the following can be stated: The invention is related to a device for removing endoprostheses having a shaft engaged in a bone cavity and coupled therein to the bone by a boundary layer made of bone tissue, connective tissue, and/or cement. In order to enable a largely traumaless and relatively simple to perform removal of the prosthesis, according to the invention a device is proposed which has an elongated body 10 having a preferably exchangeable tip 12, an elongated chisel blade 18 having a cutting edge 32 at its front end and which is guided in a thrust slide 14, 16 of the body and is disposed longitudinally slidable beyond a front face 17 of the body, as well as a driving-in member 22 which is removable coupleable to the chisel blade 18 and longitudinally slidable along the body 10 parallel to the thrust slide 14. In order to drive the chisel blade 18 into the boundary layer between the shaft of the prosthesis and the bone bearing, the driving-in member 22 is subjected to hammer strikes while the tip 12 rests with its front face against the prosthesis and the bone. Afterwards, the chisel blade is retracted from the boundary layer in the opposite direction and the process is repeated a number of times over the circumference of the prosthesis, if need be after the exchange of the chisel blade 18.

We claim:

1. A device for removing endoprostheses having a shaft engaged in a bone cavity and coupled therein to the bone by a boundary layer made of bone tissue, connective tissue, and/or cement, said device comprising a body, an elongated chisel blade having a cutting edge at its front end and which is guided in a thrust slide of the body and is disposed longitudinally slidable beyond a front face of the body, and a driving-in member which is longitudinally slidable parallel to the thrust slide, wherein the driving-in member is removably coupleable directly to the chisel blade and guided longitudinally slidable in a guide channel of the body parallel to the thrust slide, wherein the driving-in member has an engaging pin attached thereto, and wherein the body has a free space disposed therein for accepting the engaging pin, the free space being disposed at a side of the chisel blade opposing the driving-in member.

2. The device of claim 1, wherein the chisel blade is made of a flexible flat strip of tough, resilient material.

3. The device of claim 2, wherein the chisel blade is made of a flexible flat strip of resilient stainless steel.

4. The device of claim 1, wherein the cutting edge at the front end of the chisel blade is slanted or convexly curved.

5. The device of claim 1, wherein the thrust slide has at least two mutually opposed guide surfaces which abut two broadside faces and two lateral side edges of the chisel blade.

6. The device of claim 5, wherein the thrust slide is formed at least partially by two slit-like grooves which face each other with their openings and each of which embraces one lateral side edge of the chisel blade.

7. The device of claim 1, wherein the driving-in member is made of an impact resistant, steam-sterilizable synthetic material.

8. The device of claim 1, wherein the body is provided with an exchangeable tip, the body having a guide channel for the chisel blade and whose front face forms a stop and abutting surface.

9. The device of claim 8, wherein the tip is clampable to the front face of the body by way of a coupling ring.

10. The device of claim 9, wherein the coupling ring has multiple threads.

11. The device of claim 8, wherein the tip is curved in the driving-in direction toward the side of the body facing the driving-in member.

12. The device of claim 8, wherein the tip forms a stop for the driving-in member at its body-sided end.

13. The device of claim 8, wherein the body has an impact collar protruding over a surface of the body close to an end opposed to the tip.

14. The device of claim 13, wherein the impact collar is provided with an interchangeable impact plate.

15. The device of claim 14, wherein the impact plate is also formed to be a rear thrust slide cover and a stop for the chisel blade and the driving-in member.

16. The device of claim 1, wherein the driving-in member has at least one impact surface which extends substantially perpendicular to the driving-in direction.

17. The device of claim 1, wherein the chisel blade has at least one engaging point.

18. The device of claim 17, wherein the engaging pin on the driving-in member is actuatable externally.

19. The device of claim 17, wherein the engaging pin is formed by a tip of a screw which is guided in an internal screw thread of the driving-in member and which is actuatable externally.

20. The device of claim 19, wherein the screw has a knurled head which is disposed recessed in an open-edged opening of the driving-in member and accessible from two diametrically opposed sides.

21. The device of claim 17, wherein said at least one engaging point is an opening for the engaging pin attached to said driving-in member.

22. The device of claim 17, wherein said at least one engaging point is a notch element.

23. The device of claim 1, wherein the chisel blade has a thickness ranging from 0.2 to 0.6 mm.

24. The device of claim 23, wherein the chisel blade has a thickness-encoding.

25. The device of claim 1, wherein the guide channel has a dovetail shape for mating with a correspondingly shaped slide portion of the driving-in member.

26. The device of claim 1, wherein the chisel blade is longer than the body and has at least one engaging point for the engaging pin.

27. The device of claim 1, wherein the body has at least one circumferential rib extending at least partially over its circumference.

28. The device of claim 1, further comprising a handle which is removably attachable to the body and which mounts substantially perpendicular to the body.

29. The device of claim 28, wherein the handle is formed to be hollow.

30. The device of claim 1, wherein the chisel blade has a material thickness which varies in a transverse direction.

31. The device of claim 30, wherein the chisel blade has a material thickness which further varies in a longitudinal direction.

32. The device of claim 1, wherein the driving-in member is actable upon with a hammer in a driving-in direction.

33. The device of claim 1, wherein the driving-in member is coupleable to a mechanical vibrator or ultrasonic transducer whereby vibrations are transmitted to the chisel blade to assist cutting.

34. The device of claim 1, wherein the chisel blade has a material thickness which varies in a longitudinal direction.

* * * * *